(12) United States Patent
Kim et al.

(10) Patent No.: US 8,137,946 B2
(45) Date of Patent: Mar. 20, 2012

(54) RECOMBINANT GRAS STRAINS EXPRESSING THERMOPHILIC ARABINOSE ISOMERASE AS AN ACTIVE FORM AND METHOD OF PREPARING FOOD GRADE TAGATOSE BY USING THE SAME

(75) Inventors: Seong-bo Kim, Seoul (KR); Young-mi Lee, Seoul (KR); Seung-won Park, Yongin (KR); Jung-hoon Kim, Seoul (KR); Sang-hoon Song, Incheon (KR); Kang-pyo Lee, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 12/506,581

(22) Filed: Jul. 21, 2009

(65) Prior Publication Data

US 2010/0041106 A1   Feb. 18, 2010

Related U.S. Application Data

(63) Continuation-in-part of application No. 11/564,936, filed on Nov. 30, 2006, now abandoned.

(30) Foreign Application Priority Data

Nov. 27, 2006   (KR) .................. 10-2006-0117792

(51) Int. Cl.
   *C12N 9/90* (2006.01)
   *C07H 21/02* (2006.01)
(52) U.S. Cl. ...................... 435/233; 536/23.1
(58) Field of Classification Search .............. None
   See application file for complete search history.

(56) References Cited

FOREIGN PATENT DOCUMENTS

| KR | 1020000073075 | 12/2000 |
|---|---|---|
| KR | 10-2002-0051835 | 6/2002 |
| KR | 10-2004-0058544 | 7/2004 |
| KR | 1020060068505 | 6/2006 |
| WO | 02/052021 | 7/2002 |
| WO | 2008/066260 | 6/2008 |

OTHER PUBLICATIONS

Archer et al., The genome sequence of *E. coli* W (ATCC 9637): comparative genome analysis and an improved genome-scale reconstruction of *E. coli*., 2011 BMC Genomics 2011, vol. 12:9, pp. 1-20.*
Schallmey et al., Developments in the use fo *Bacillus* species for industrial production., Can. J. Microbiol., 2004, vol. 50, pp. 1-17.*
Kimura et al., Triggering Mechanism of L-Glutamate Overproduction by DtsR1 in Coryneform Bacteria, Journal of Bioscience and Bioengineering, 2002, vol. 94, pp. 545-551.*

(Continued)

*Primary Examiner* — Alexander Kim
(74) *Attorney, Agent, or Firm* — Occhiuti Rohlicek & Tsao LLP

(57) ABSTRACT

The present invention relates to a recombinant GRAS (Generally Recognized As Safe) strains expressing thermophilic arabinose isomerase as an active form and method of food grade tagatose by using the same, and more precisely, a gene encoding arabinose isomerase originating from the thermophilic *Geobacillus stearothermophilus* DSM22 and *Geobacillus thermodenitrificans*, a recombinant expression vector containing the gene, a recombinant GRAS strains expressing the thermophilic arabinose isomerase as an active form by transformed with the expression vector, and a method of preparing food grade tagatose from galactose by using the same.

9 Claims, 8 Drawing Sheets

OTHER PUBLICATIONS

Kim, P. "Current Studied on biological tagatose production using L-arabinose isomerase: a review and future perspective". Applied Microbiology and Biotechnology, 2004, vol. 65, pp. 243-249.

Office Action in connection with Australian Application No. 2007326190 dated Nov. 22, 2010, 4 pages.

Supplementary European Search Report for European Application No. EP 07 83 4204, dated Feb. 4, 2010, 4 pages.

Lee, Sang-Jae et al., "Characterization of a Thermoacidophilic L-Arabinose Isomerase from Alicyclobacillus acidocaldarius: Role of Lys-269 in pH Optimum." Applied and Environmental Microbiology, vol. 71, No. 12, Dec. 2005, pp. 7888-7896.

Westers et al., "*Bacillus subtilis* as cell factory for pharmaceutical proteins: a biotechnological approach to optimize the host organism." Biochimica et Biophysica Acta, vol. 1694, No. 1-3, Nov. 11, 2004, pp. 299-310.

Srivastava, Preeti et al., "Gene expression systems in corynebacteria." Protein Expression and Purification, Academic Press, vol. 40, No. 2, Apr. 1, 2005, pp. 221-229.

Cheon, Jina et al. "Characterization of L-Arabinose Isomerase in *Bacillus subtilis*, a GRAS Host, for the Production of Edible Tagatose." Food Biotechnology, vol. 23, No. 1, 2009, pp. 8-16.

Kim et al., A feasible enzymatic process for D-Tagatose production by an immobilized thermostable L-Arabinoase isomerase in a packed-bed bioreactor, Biotechnol. Prog., 19:400-404 (2003).

Kim et al., Purification and characterization of an L-arabinoase isomerase from an isolated strain of geobacillus thermodenitrificans producing D-tagatose, Journal of Biotechnology, 120:162-173 (2005).

Hudault et al., *Escherichia coli* strains colonizing the gastrointestinal tract protect germfree mice salmonella typhimurium infection, Gut, 49:47-55. (2001).

NCBI reference, *Geobacillus stearothermophilus*, Taxonomy ID: 1422, viewed on Mar. 20, 2008.

Microbiology On-line, *E.coli* K-12-model Not menace in schoolwork, viewed on Mar. 20, 2008.

Lee, S.J., et al. Characterization of a Thermoacidophilic L-Arabinose Isomerase from *Alicyclobacillus acidocaldarius*: Role of Lys-269 in pH Optimum, Dec. 2005, Applied and Environmental Microbiology; vol. 71, pp. 7888-7896.

Office Action in connection with New Zealand application No. 576797 dated Jul. 23, 2010, 7 pages.

Office Action in connection with New Zealand application No. 576796 dated Jul. 23, 2010, 6 pages.

* cited by examiner

[Figure 3]
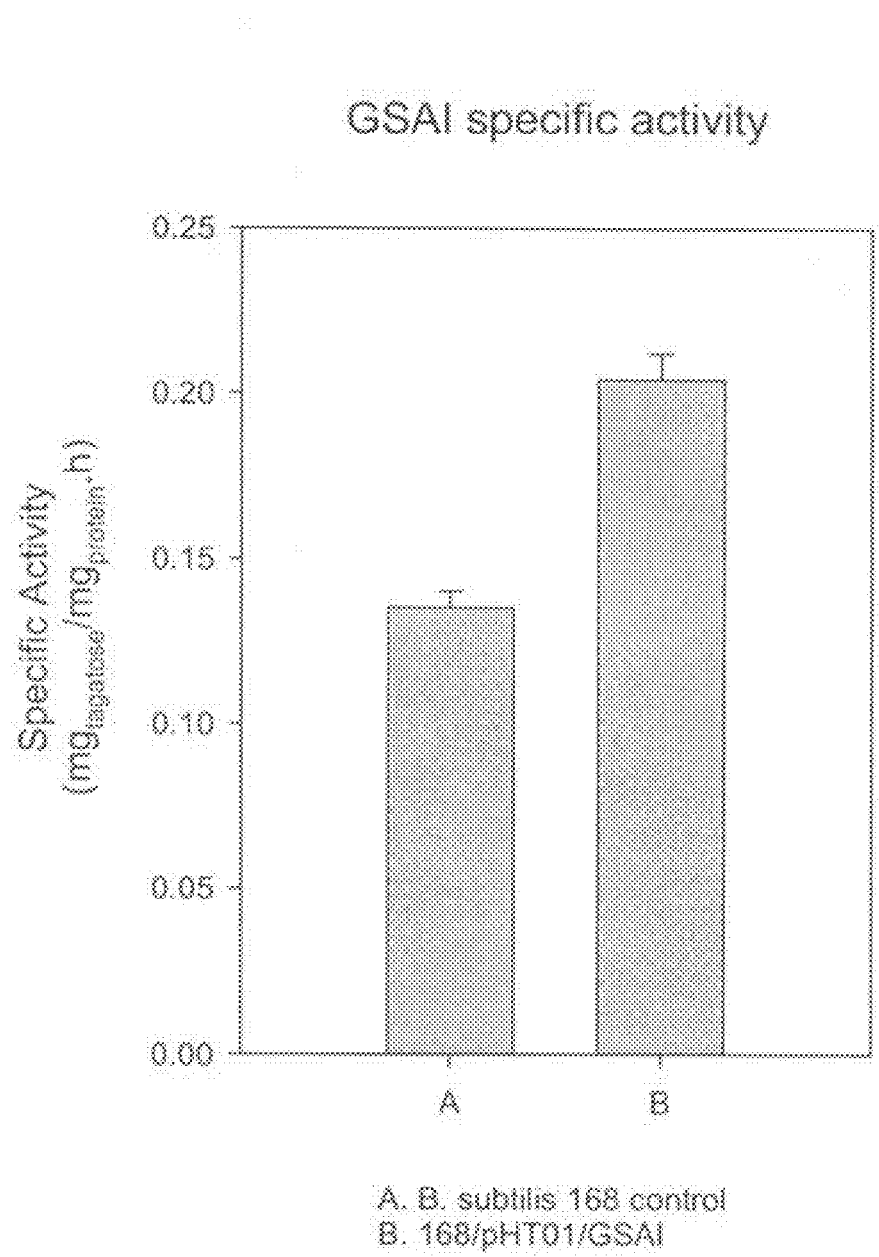

[Figure 4]
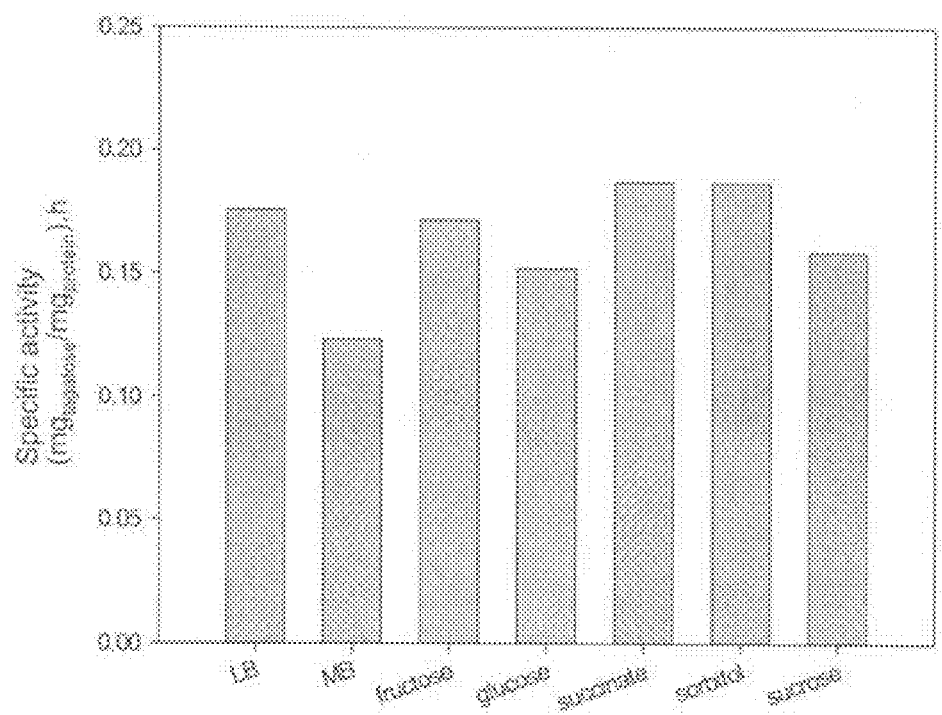

[Figure 5]
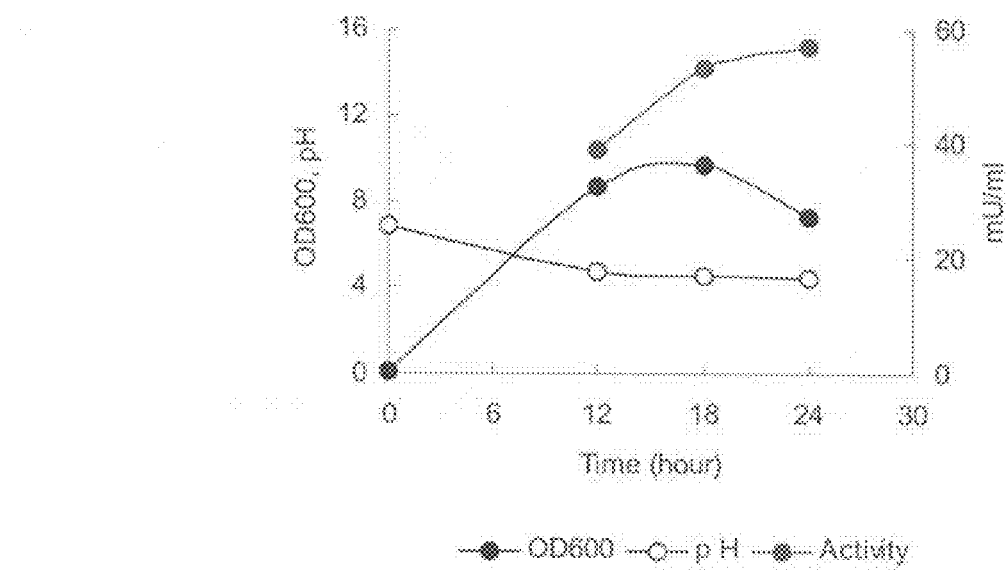
[Figure 6]
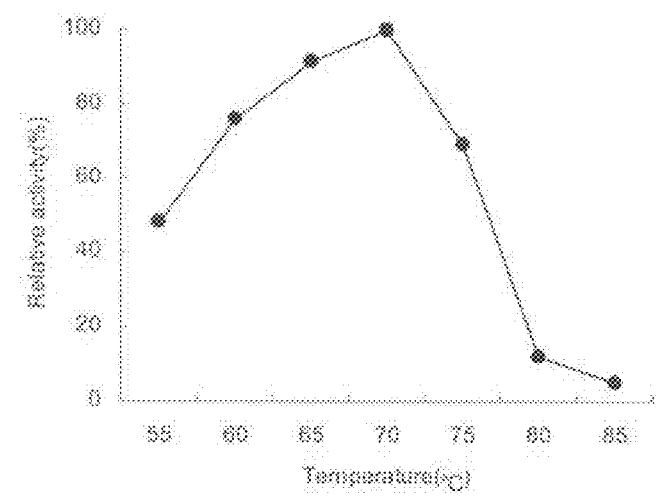

[Figure 7]
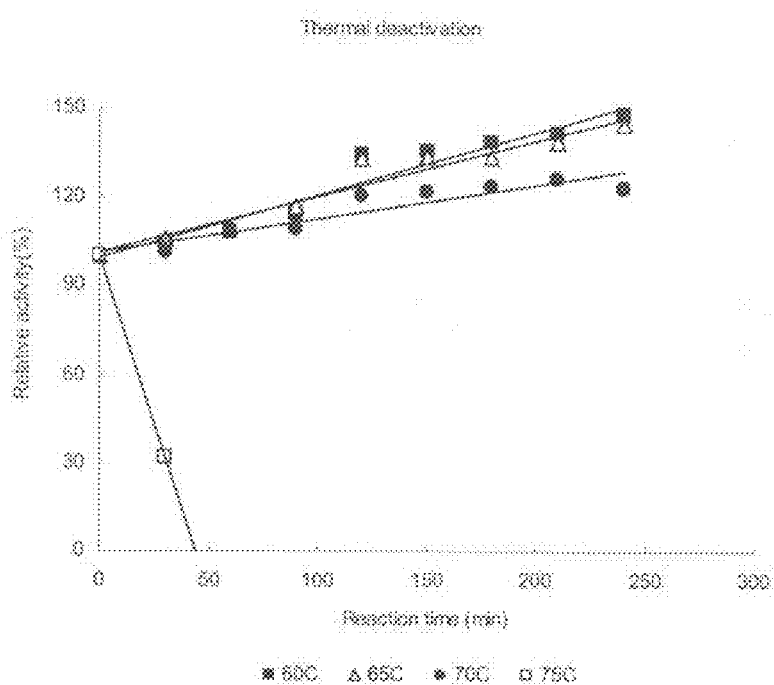
[Figure 8]
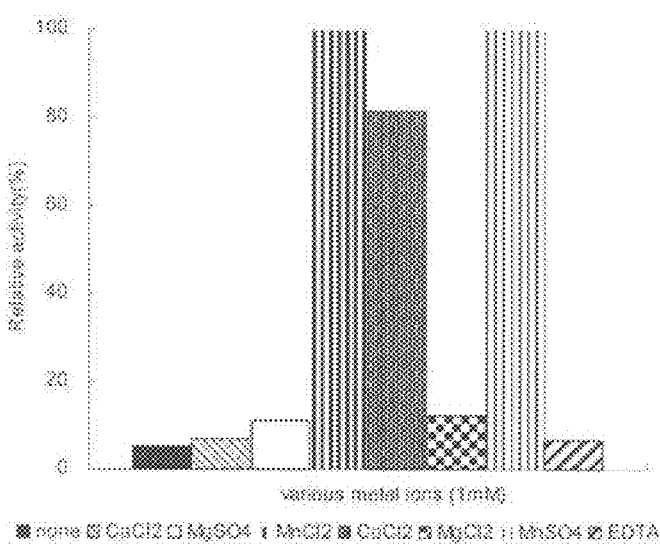

[Figure 9]
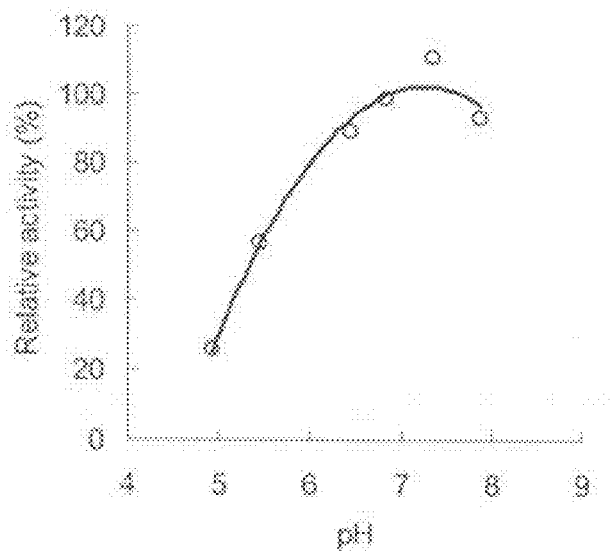
[Figure 10]
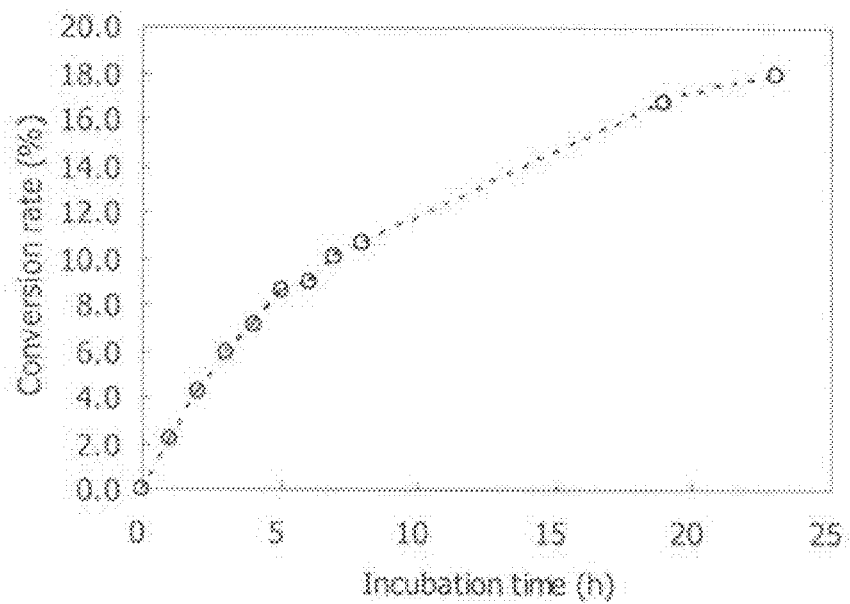

[Figure 11]
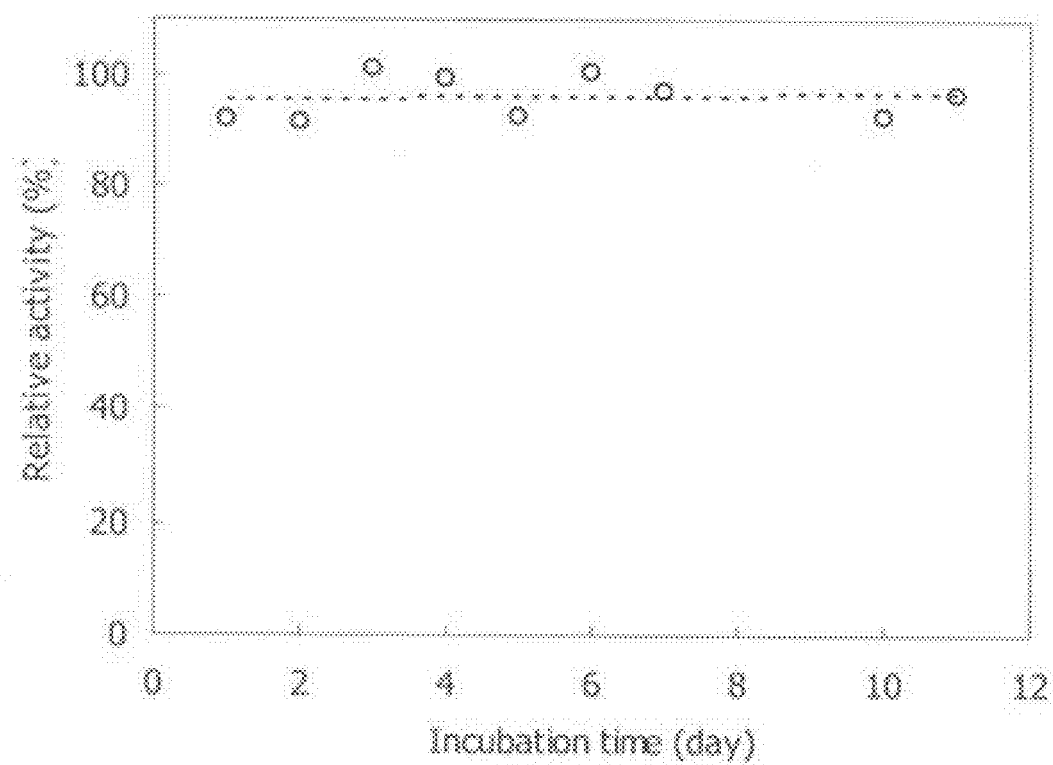

```
                          SEQUENCE LISTING

<160> NUMBER OF SEQ ID NOS: 8

<210> SEQ ID NO 1
<211> LENGTH: 38
<212> TYPE: DNA
<213> ORGANISM: Artificial Sequence
<220> FEATURE:
<223> OTHER INFORMATION: Synthetic primer

<400> SEQUENCE: 1
tctagaatga tgctgtcatt acgtccttat gaattttg                            38

<210> SEQ ID NO 2
<211> LENGTH: 35
<212> TYPE: DNA
<213> ORGANISM: Artificial Sequence
<220> FEATURE:
<223> OTHER INFORMATION: Synthetic primer

<400> SEQUENCE: 2
tctagattac cgcccccgcc aaaacacttc gttcc                               35

<210> SEQ ID NO 3
<211> LENGTH: 31
<212> TYPE: DNA
<213> ORGANISM: Artificial Sequence
<220> FEATURE:
<223> OTHER INFORMATION: Synthetic primer

<400> SEQUENCE: 3
cccgatatca tgctgtcatt acgtccttat g                                   31

<210> SEQ ID NO 4
<211> LENGTH: 31
<212> TYPE: DNA
<213> ORGANISM: Artificial Sequence
<220> FEATURE:
<223> OTHER INFORMATION: Synthetic primer

<400> SEQUENCE: 4
tgcactgcag ttaccgcccc cgccaaaaca c                                   31

<210> SEQ ID NO 5
<211> LENGTH: 29
<212> TYPE: DNA
<213> ORGANISM: Artificial Sequence
<220> FEATURE:
<223> OTHER INFORMATION: Synthetic primer

<400> SEQUENCE: 5
cccgatatca tgatgctgtc attacgtcc                                      29

<210> SEQ ID NO 6
<211> LENGTH: 32
<212> TYPE: DNA
<213> ORGANISM: Artificial Sequence
<220> FEATURE:
<223> OTHER INFORMATION: Synthetic primer

<400> SEQUENCE: 6
tgcactgcag ttaccgcccc cgccaaaaca cc                                  32
```

<210> SEQ ID NO 7
<211> LENGTH: 1560
<212> TYPE: DNA
<213> ORGANISM: Geobacillus stearothermophilus DSM 22

<400> SEQUENCE: 7

| | | | | | |
|---|---|---|---|---|---|
| aaagaattta | tgagtttatg | gtgaacgggg | aggagcaatg | atgctgtcat | tacgtcctta | 60 |
| tgaattttgg | tttgtaacgg | gaagccagca | cttgtacgga | gaagaagcat | taaagcaagt | 120 |
| tgaagagcat | tcaatgatga | ttgtcaatga | gctgaatcaa | gattcagtgt | tcccgttccc | 180 |
| acttgttttc | aaatcagttg | tcacaacgcc | agaggaaatc | cggcgcgttt | gccttgaggc | 240 |
| gaatgcgagc | gaacaatgcg | ctggggtcat | cacttggatg | catacattct | cgccagcgaa | 300 |
| gatgtggatt | ggcggccttt | tggagctgcg | aaaaccgtta | ttgcatcttc | acactcaatt | 360 |
| taaccgtgat | attccgtggg | acagcatcga | tatggacttt | atgaacttaa | accaatcggc | 420 |
| tcacggtgac | cggaatacg | gatttatcgg | cgcgagaatg | ggcgtggccc | ggaaagtggt | 480 |
| ggtcgggcac | tgggaagacc | cagaagtccg | cgagcggctg | gcgaaatgga | tgcggacggc | 540 |
| tgtcgcgttt | gcggaaagcc | gcaacctaaa | agtggctcgt | tttggcgaca | catgcgtga | 600 |
| agtggctgtg | acggaagggg | acaaagtcgg | agcgcaaatt | caattcggct | ggtcggtcaa | 660 |
| cggctatggc | atcgggatt | tggtgcaata | catccgcgat | gtttctgaac | aaaaagtgaa | 720 |
| cgagttgctc | gatgaatacg | aggagctgta | cgacattgta | cccgccggcc | gccaagaagg | 780 |
| gcccgttcgc | gaatcaattc | gtgaacaggc | gcggattgaa | ctcgggctga | agccttttt | 840 |
| gcaggatggg | aactttaccg | ctttcacgac | gacgttcgag | gacttgcatg | ggatgaagca | 900 |
| gctcccggga | cttgccgttc | agcgactcat | ggcggaagga | tacggttttg | gaggcgaggg | 960 |
| agactggaaa | acggctgcgc | ttgtccggct | aatgaaagtg | atggctgatg | gaaaagggac | 1020 |
| gtcatttatg | gaagattaca | cgtaccacct | tgagccgggt | aatgaaatga | ttcttggcgc | 1080 |
| ccacatgttg | gaagtatgcc | cgactattgc | agcgacccgg | ccgcgaatcg | aagtccatcc | 1140 |
| gctttccatc | ggtggaaaag | aagatccagc | ccgtctcgtg | tttgacggcg | gcgagggtgc | 1200 |
| ggcggtcaac | gcgtcattga | tcgacttagg | gcaccgtttc | cgactcatcg | tcaatgaagt | 1260 |
| cgatgcggtg | aaaccggaac | acgacatgcc | gaaattacca | gtcgcccgca | ttttatggaa | 1320 |
| gcctcgcccg | tcgctccgcg | actccgctga | agcatggatt | ttagctggcg | gcgcccacca | 1380 |
| tacgtgcttc | tcatttgcgg | ttacaacaga | acagctgcaa | gactttgcgg | aaatggcagg | 1440 |
| gattgaatgt | gtcgtgatca | tgaacatac | gtccgtctcg | tccttcaaaa | atgaactgaa | 1500 |
| atggaacgaa | gtgttttggc | gggggcggta | agatttcacg | tgcagatccg | taatatgacg | 1560 |

<210> SEQ ID NO 8
<211> LENGTH: 1494
<212> TYPE: DNA
<213> ORGANISM: Geobacillus thermodenitrificans

<400> SEQUENCE: 8

| | | | | | |
|---|---|---|---|---|---|
| atgatgctgt | cattacgtcc | ttatgaactt | tggtttgtga | caggaagcca | gcacttatac | 60 |
| ggggaagaag | cgttaaaaca | agttgaagaa | cattcaagaa | cgatcgtcaa | tgagttgaac | 120 |
| cgtgattcgg | tgtttccgtt | cccactcgtt | ttcaaaccga | tcgtcacaac | cccagaagaa | 180 |
| attcgcaaca | tctgtcttga | ggcgaatgcg | agcgaacaat | gtgccggcgt | tgtcacatgg | 240 |
| atgcatacgt | tctcgccagc | gaagatgtgg | attggcggcc | ttttggagtt | gcgaaaaccg | 300 |
| ttattgcatc | ttcacactca | gtttaaccgt | gatattccgt | gggacagcat | cgatatggac | 360 |

```
tttatgaact taaaccaatc ggctcacggt gaccgagaat acggatttat cggtgcgaga    420
atgggagttg cccggaaagt cgtcgttggt cattgggaag acccagaagt ccgcgagcgg    480
ctggcgaaat ggatgcggac ggccgtcgcc tttgcggaaa gtcgacatct taaagttgcc    540
cgtttcggcg ataacatgcg tgaagtggcg gtaacgaag gggacaaagt gggagcgcaa    600
attcaattcg gctggtcgat caacggttat ggcattgggg atttggtgca atctattcgc    660
gatgtttctg aacaaagcgt caacgaactg cttgatgaat atgctgaact atatgacatt    720
gtacctgctg gccgtcaaga tggacccgtt cgtgagtcga tccgtgagca ggcgcggatt    780
gagcttgggt taaaagcatt tttgcaagac gggaacttca ctgcctttac gacgacgttt    840
gaagatttgc acggcatgaa gcaacttcca ggactagcgg ttcaacggct tatggcagag    900
ggatatggat ttggcggcga aggcgactgg aaaacggctg ctctcgttcg gttgatgaaa    960
gtcatggcgg atggcaaagg aacatcgttc atggaagact acacgtacca ctttgagccg   1020
ggcaacgaaa tgattcttgg cgctcatatg ctcgaagtat gcccgacgat cgcagcaacg   1080
cgaccgcgca tcgaagttca tccgctttcg attggtggaa aagaagatcc agcccgtctc   1140
gtgtttgacg gcggtgaggg cgcagcggtc aatgcttcgc tgattgactt agggcaccgt   1200
ttccgtctca ttgtcaatga agtcgatgcg gtgaaaccgg aatacgacat gccgaaattg   1260
ccggttgccc gtattttatg gaaaccgcgc ccgtcgttgc gtgattcagc tgaagcatgg   1320
attttagccg gcggtgctca tcacacaagc ttctcgtttg ccgtcacggc tgaacagctg   1380
gaagactttg cggaaatgac cggcattgaa tgtgtcgtga tcaaagaaca tacttccgtc   1440
tcgtcattca aaaacgaact gaggtggaat gaggtgtttt ggcgggggcg gtaa         1494
```

RECOMBINANT GRAS STRAINS EXPRESSING THERMOPHILIC ARABINOSE ISOMERASE AS AN ACTIVE FORM AND METHOD OF PREPARING FOOD GRADE TAGATOSE BY USING THE SAME

CROSS-REFERENCE TO RELATED APPLICATION

This application is a continuation-in-part and claims the benefit of the priority pursuant to 35 U.S.C. §119(e) of U.S. application Ser. No. 11/564,936, filed Nov. 30, 2006, which claims priority of Korean Application No. 10-2006-0117792, filed Nov. 27, 2006.

TECHNICAL FIELD

The present invention relates to a recombinant GRAS (Generally Recognized As Safe) strains expressing thermophilic arabinose isomerase as an active form and method of food grade tagatose by using the same, and more precisely, a gene encoding arabinose isomerase originating from the thermophilic *Geobacillus stearothermophilus* DSM22 and *Geobacillus thermodenitrificans*, a recombinant expression vector containing the gene, a recombinant GRAS strains expressing the thermophilic arabinose isomerase as an active form by transformed with the expression vector, and a method of preparing food grade tagatose from galactose by using the same.

BACKGROUND ART

With the increasing interest in well-being or a healthy life, tagatose has been proposed as an alternative to sugar as it has less side effects and sugar is one of the major factors causing various adult diseases. Tagatose is the isomer of galactose and is known to have fructose-like physiochemical properties. Tagatose is a natural low-calorie sugar, and has recently been approved by the FDA in the USA as GRAS (Generally Recognized As Safe), so it is now allowed to be added as a sweetener to foods, beverages, health foods, diet additives, etc.

GRAS indicates a substance that is generally recognized as safe, which is judged by specialized people having enough experience and skills through scientific procedure and examination under the indicated conditions and purpose of use. GRAS is a unique system used only in the USA to evaluate the safety of foods and food chemical substances (under certain conditions), but it is recognized world-wide.

Tagatose is produced by either isomerization, which is a chemical method using a catalyst to produce an isomer, of galactose or a biological method using isomerase to convert galactose enzymatically.

One of the biological methods well-known to those in the art is to convert aldose or aldose derivatives into ketose or ketose derivatives by using an enzyme. The isomerization of galactose into tagatose using arabinose isomerase is generally carried out thermodynamically at high temperature and exhibits a proportionally high conversion rate. Therefore, developing an enzyme that works stably at high temperature and a method of preparing tagatose using the same are key techniques for the industrial application thereof based on the biological conversion of tagatose using an isomerase. By screening thermophile derived arabinose isomerases, an industrially applicable thermophilic isomerase has been tried, and efforts have also been made by many research teams to establish an isomerization process using the same.

In Korea, an enzymatic isomerization method using arabinose isomerase has been developed by Tong Yang Confectionery Corp. According to the method, an *E. coli* derived arabinose isomerase gene was mass-expressed in *E. coli* by recombinant technology. This recombinant isomerase was reacted at 30° C. for 24 hours to convert galactose into tagatose, and at this time the conversion rate was 25%, indicating that both thermostability and transformation yield were very low (Korean Patent Application No. 99-16118). Professor Oh and his colleagues (Sejong University) succeeded in the mass-expression of arabinose isomerase originating from *Geobacillus stearothermophilus* in *E. coli* by recombinant technology, and based on that they proposed an isomerization procedure at high temperature to convert galactose into tagatose. Tong Yang Confectionery Corp. team separated a thermophilic isomerase from a hot spring area by screening the thermophilic microorganism library and then expressed it as an active form in a recombinant *E. coli* host to use galactose for the high temperature isomerization process. Similarly, CheBiGen Inc. also produced thermophilic isomerase originating from *Geobacillus dinitrificans* DBG-A1 in *E. coli* and developed a technique to produce tagatose by immobilization using the same.

The expression level of the isomerase originating from the *Geobacillus* microorganism is too low to be applied in industry. The production of tagatose using a thermophile derived arabinose isomerase still depends on the method of using a recombinant enzyme mass-expressed in recombinant *E. coli* or the isomerization of galactose into tagatose using a host containing the recombinant enzyme. However, this biotechnological production of tagatose using recombinant *E. coli* is not appropriate for the production of tagatose as a food material. To produce tagatose as a food additive, arabinose isomerase expressed in a host which is a GRAS microorganism appropriate for the mass-production of the same is essential.

Industrially applicable GRAS microorganisms for the production of a recombinant enzyme can be selected from a group consisting of *Bacillus* sp., *Corynebacterium* sp., and *Lactobacillus* sp. It is easy to manipulate the genes of *Bacillus* sp. and *Corynebacterium* sp. strains for industrialization and mass-culture, and they are highly stable under various conditions. In fact, among GRAS microorganisms, mostly *Bacillus* sp. and *Corynebacterium* sp. strains have been used as a host for the production of a recombinant enzyme.

The present inventors succeeded in expressing thermophilic arabinose isomerase originating from *Geobacillus* sp. as an active form in GRAS strains such as *Bacillus* sp. and *Corynebacterium* sp. strains. The present inventors further established a method to induce isomerization of galactose into tagatose at high concentration by using the recombinant GRAS strains.

DISCLOSURE OF THE INVENTION

It is an object of the present invention to express thermophilic arabinose isomerase originating from *Geobacillus* sp. as an active form from GRAS strains and to provide a method of preparing food grade tagatose by isomerization of galactose.

The above object of the present invention can be achieved by the following embodiments of the present invention.

To achieve the above objects, the present invention provide a gene encoding thermophilic arabinose isomerase originating from the thermophilic *Geobacillus stearothermophilus* DSM22 and *Geobacillus thermodenitrificans*, a recombinant expression vector containing the gene, a recombinant GRAS microorganisms expressing thermophilic arabinose isomerase as an active form by transformed with the expression vector.

And, the present invention also provide a method of preparing food grade tagatose from galactose by using the same.

Hereinafter, the present invention is described in detail.

GRAS (Generally Recognized As Safe) strains of the present invention preferably include *Bacillus* sp. and *Corynebacterium* sp. strains, and *Corynebacterium glutamicum* KCTC 13032 and *Bacillus subtilis* 168 are more preferred.

The gene encoding thermophilic arabinose isomerase of the present invention preferably originates form a thermophile, and more preferably originates from *Geobacillus stearothermophilus* DSM22 or *Geobacillus thermodenitrificans* (Biotechnology letters, Volume 28, Number 3, February 2006, pp. 145-149(5)).

The arabinose isomerase gene of the present invention can be modified by those in the art using any conventional mutagenesis method such as directed evolution and site-directed mutagenesis. Thus, any host cells that have a certain level of homology with a GRAS host, for example at least 70% but preferably at least 80% and more preferably at least 90% homology with a GRAS host, a recombinant enzyme that is expressed as an active form in the host and any host cells containing the enzyme are all included in the criteria of the present invention.

Embodiments of the present invention also provide a vector containing a gene encoding the arabinose isomerase of the present invention. The vector of the present invention is a typical vector for cloning or expression. The vector is not limited to a specific one and any vector known to those in the art is acceptable.

In the present invention, a promoter which is active in *Bacillus* sp. and *Corynebacterium* sp. was used in the vector to express a thermophilic arabinose isomerase as an active form. In a preferred aspect of the present invention, a recombinant shuttle vector PHT01(PBS001) which containing Pgrac promoter for *Bacillus* sp. and a recombinant shuttle vector pCJ-1(KCCM-10611) which containing pcj1 promoter for *Corynebacterium* sp. was used, respectively.

The promoter sequence used for the gene expression in the *Corynebacterium* has not been identified unlike other promoters used in industrial microorganisms such as *E. coli* or *Bacillus subtilis*. Herein, a strong promoter that originates from *Corynebacterium* sp., a popular industrial microorganism, and is able to be expressed in *E. coli* has been developed. Tac promoter is known as being one of the strongest promoters. Tac promoter is prepared by fusion of a sequence of the −35 region of the tryptophane operon promoter of *E. coli* with a sequence of the −10 region of the lactose operon promoter of *E. coli*. The pcj1 promoter in the present invention was confirmed to be more effective in expressing a target gene than tac promoter in *Corynebacterium* sp. bacteria cells (Korean Patent Publication No. 10-2006-0068505).

The promoter for *Bacillus* sp. of the present invention exhibits promoter activity not only in *Bacillus* sp. but also in *Lactobacillus* sp. such as *Lactobacillus* and *Bifidobacterium*. The promoter for *Corynebacterium* sp. also exhibits promoter activity in both *Corynebacterium* sp. and *Escherichia* sp. bacteria, and *E. coli* cells. In particular, the promoter of the present invention showed promoter activity twice as strong in *Escherichia* sp. bacteria cells as tac promoter did.

The present invention provide a recombinant *Bacillus* sp. and *Corynebacterium* sp. strain by transformed with the vector. Preferably, the recombinant strain may be a recombinant *Bacillus subtilis* GSAIB-1(KCCM-10789P), *Corynebacterium glutamicum* GSAIC-1(KCCM-10788P) and *Corynebacterium glutamicum* mGTAIC001(KCCM-11018P).

The present invention also provide a method of preparing food grade tagatose by culturing the recombinant GRAS strain using galactose as a substrate.

In the present invention, tagatose is produced by using the activity of thermophilic arabinose isomerase expressed in the recombinant GRAS strains in the high temperature (over 50° C.) which is impossible to growth of microorganisms. That is, tagatose in the present invention is not produced by fermentation (i.p. metabolism) but produced by enzyme conversion reaction.

In the view of the economic efficiency and the stability of operation in the enzyme production, it is obvious that the method using the enzyme which is separated, purified and immobilized from the strain is less economic efficiency than the method using directly the immobilized microbial cells. Therefore, it is important to reduce the cost of separating and purifying the enzyme by extracellular release of the arabinose isomerase expressed in the recombinant strain as an active form.

In the present invention, to use of immobilized GRAS microorganisms, especially *Bacillus* sp. and *Corynebacterium* sp which is gram positive bacteria with a solid cell wall, used as strain is substantially used as a dead bacteria.

The bacterial cell wall itself is a type of encapsulation because the enzyme entrapped inside it. Therefore, in the preferred aspect of the present invention, the microbial immobilization, especially the method of immobilization using crosslinker such as alginate is used to encapsulating and molding strains as a carrier having appropriate size and property for use in the operation.

The galactose with relatively small molecular weight is transferred into the strain through passive diffusion by concentration gradient, then it is converted to tagatose by thermal arabinose isomerase which is presented in the strain, finally the tagatose is transferred to the extracellular matrix of the strain by passive diffusion.

In the present invention, it is confirmed that release and inactivation of enzyme which is the largest disadvantage of cell immobilization is effectively controlled by continuous operation of bioreactor (see FIG. 11). Therefore, the enzyme expressed in the GRAS strain of the present invention can be stably used under severe operating condition such as high glucose concentration and high operating temperature because of the cell wall of *Bacillus* sp. and *Corynebacterium* sp. which is relatively solid and dense.

BRIEF DESCRIPTION OF THE DRAWINGS

The application of the preferred embodiments of the present invention is best understood with reference to the accompanying drawings, wherein:

FIG. 3 is a graph illustrating the enzyme activity of the thermophilic arabinose isomerase generated in the recombinant *Bacillus* host cells. A indicates the enzyme activity measured in a crude enzyme solution obtained from the culture of the host cells (*Bacillus subtilis* 168) only, and B indicates the enzyme activity measured in a crude enzyme solution obtained from the culture of the recombinant *Bacillus* host cells (GSAIB-1) containing the shuttle vector harboring the arabinose isomerase gene, FIG. 4 is a graph illustrating the optimum conditions for the expression of the recombinant strain GSAIB-1 and the optimum conditions for the enzyme activity, FIG. 5 is a graph illustrating the growth of the recombinant strain GSAIC-1 in the optimum medium.

FIG. 6 is a graph illustrating the activity of the purified arabinose isomerase originated from the recombinant *Corynebacterium glutamicum* mGTAIC001 at various temperature.

FIG. 7 is a graph illustrating the thermal stability of the enzyme according to with and without $MnCl_2$.

FIG. 8 is a graph illustrating the effect of various metal ion to the thermal stability of the enzyme.

FIG. 9 is a graph illustrating the maximum pH of the enzyme.

FIG. 10 is a graph illustrating the tagatose productivity at various time in the microbial immobilized bioreactor.

FIG. 11 is a graph illustrating the stability of enzyme activity in the microbial immobilized bioreactor.

BEST MODE FOR CARRYING OUT THE INVENTION

Figure 1:
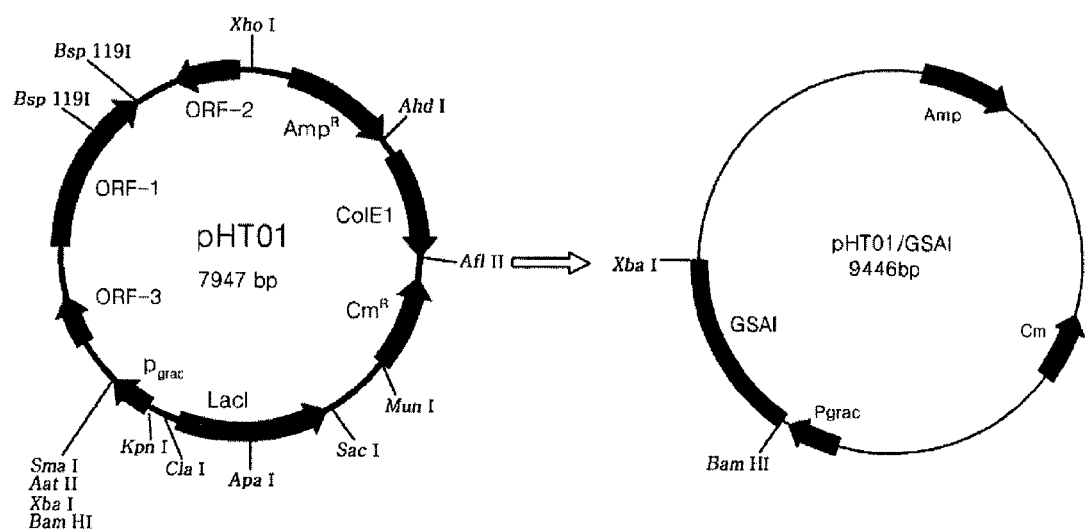
FIG. 1 is a schematic diagram illustrating the construction of the recombinant expression vector pHT01-GSA1 containing a gene encoding the thermophilic arabinose isomerase originating from the *Geobacillus stearothermophilus* DSM 22 strain.

Practical and presently preferred embodiments of the present invention are illustrated as shown in the following examples.

However, it will be appreciated that those skilled in the art, on consideration of this disclosure, may make modifications and improvements within the spirit and scope of the present invention.

EXAMPLES

In the preferred embodiment of the present invention, a gene encoding thermophilic arabinose isomerase originating from the hyperthermophilic *Geobacillus stearothermophilus* DSM 22 was inserted into pCJ-1 (*E. coli-Corynebacterium* shuttle vector, Korean Patent Publication No. 10-2006-0068505) and pHT10 (*E. coli-Bacillus* shuttle vector, Mo Bi Tech., Goettingen, Germany). *Corynebacterium glutamicum* KCTC 13032 and *Bacillus subtilis* 168 were transformed with the above vectors, in which the arabinose isomerase was finally expressed as an active form.

And, a gene encoding thermophilic arabinose isomerase originating from the hyperthermophilic *Geobacillus thermodenitrificans* was inserted into pCJ-1 (*E. coli-Corynebacterium* shuttle vector, Korean Patent Publication No. 10-2006-0068505). *Corynebacterium glutamicum* KCTC 13032 was transformed with the above vectors, in which the arabinose isomerase was finally expressed as an active form.

The recombinant strains *Bacillus subtilis* GSAIB-1, *Corynebacterium glutamicum* GSAIC-1 and *Corynebacterium glutamicum* mGTAIC001 were each cultured and cell extracts were obtained from each stage of the cell culture. The production activity of tagatose was determined by measuring the amount of active recombinant protein stage by stage. The optimally expressed resultant culture was separated and purified by cell lysis, heat treatment. The production activity of tagatose was confirmed by the measurement of the protein activity.

Example 1

Cloning of the Arabinose Isomerase

*Geobacillus stearothermophilus* DSM 22 was cultured under aerobic conditions. Centrifugation was performed at 8,000×g for 10 minutes to recover the cultured cells. Genomic DNA was extracted from the obtained cells by using a Cell culture DNA Midi Kit (Qiagen, U.S.A.). Polymerase Chain Reaction (PCR) was performed with the genomic DNA by using oligonucleotides 5'-TCTAGAATGATGCTGTCAT-TACGTCCTTATGAATTTTG-3' (SEQ. ID. NO: 1) and 5'-TCTAGATTACCGCCCCCGCCAAAACACT-TCGTTCC-3' (SEQ. ID. NO: 2) with the insertion of XbaI and BamHi restriction enzyme site sequences as primers. PCR product 1 was obtained by amplifying the 1494 bp DNA containing the arabinose isomerase gene originating from *Geobacillus stearothermophilus*. PCR was performed again with the genomic DNA by using oligonucleotides 5'-CCCGAT ATCATGCTGTCATTACGTCCTTATG-3' (SEQ. ID. NO: 3) and 5'-TGCACTGCAGTTACCGC-CCCCG CCAAAACAC-3' (SEQ. ID. NO: 4) with the insertion of EcoRV and PstI restriction enzyme site sequences as primers. PCR product 2 was obtained by amplifying 1512 bp DNA containing the arabinose isomerase gene originating from *Geobacillus stearothermophilus*.

Also, Polymerase Chain Reaction (PCR) was performed with the plasmid DNA containing the arabinose isomerase gene originating from *Geobacillus thermodenitrificans* by using oligonucleotides 5'-CCCGATATCATGATGCTGT-CATTACGTCC-3' (SEQ. ID. NO: 5) and 5'-TGCACTG-CAGTTACCGCCCCCGCCAAAACACC-3' (SEQ. ID. NO: 6) with the insertion of EcoRV and PstI restriction enzyme site sequences as primers. PCR product 3 was obtained by amplifying the 1494 bp DNA containing the arabinose isomerase gene originating from *Geobacillus thermodenitrificans*.

To over-express the arabinose isomerase encoded by the above three amplified genes, shuttle vector pHT01 originating from *Bacillus* sp. and shuttle vector pCJ-1 originating from *Corynebacterium* sp. were used. The shuttle vector pCJ-1 was introduced into *E. coli* DH5alpha, which was deposited on Nov. 6, 2004 at the Korean Culture Center of Microorganisms (KCCM), 361-221, Yurim B/D, Hongje-1-dong, Seodaemun-gu, Seoal 120-091, Republic of Korea, an International Depositary Authority (IDA), and has assigned an Accession No: KCCM-10611. The shuttle vector pHT01 was obtained from Mo Bi Tech Co. (PBS001) (Table 1).

TABLE 1

| Vector | Promoter | Vector | Accession/ distribution No. | Derived protein |
| --- | --- | --- | --- | --- |
| pCJ-1 | Pcj1 | pECCG117 | KCCM-10611 | Heat-shock protein hsp60 |
| pHT01 | Pgrac | — | PBS001 | — |

Figure 2:
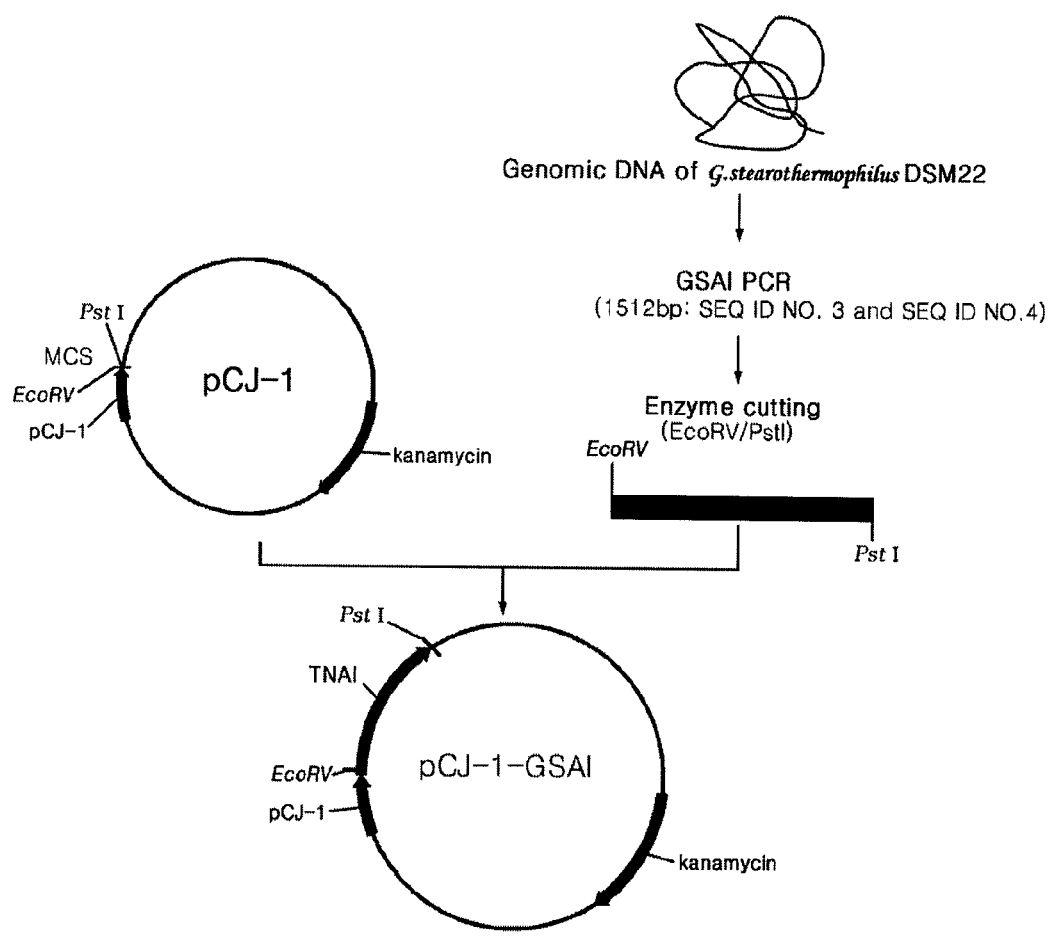
FIG. 2 is a schematic diagram illustrating the construction of the recombinant expression vector pCJ-1-GSAI containing a gene encoding the thermophilic arabinose isomerase originating from the *Geobacillus stearothermophilus* DSM 22 strain.

PCR product 1, digested by restriction enzymes XbaI and BamHI, was inserted into the shuttle vector pHT01, which was digested by the same enzymes, leading to the construction of the recombinant expression vector pHT01-GSAI (see FIG. 1). PCR product 2 and 3, digested with restriction enzymes EcoRV and PstI, were inserted into the shuttle vector pCJ-1, which was digested with the same restriction enzymes, leading to the construction of the recombinant expression vector pCJ-1-GSA1 and pCJ-1-mGTAI (see FIG. 2).

*Bacillus subtilis* 168 and *Corynebacterium glutamicum* KCTC 13032 were each transformed with the recombinant expression vectors pHT01-GSA1, pCJ-1-GSA1 or pCJ-1-mGTAI to prepare recombinant strains, which were named '*Corynebacterium glutamicum* GSAIC-1', '*Bacillus subtilis* GSAIB-1' and '*Corynebacterium glutamicum* mGTAIC001'. The recombinant strains were deposited at the Korean Culture Center of Microorganisms (KCCM), an International Depositary Authority (IDA), addressed at #361-221, Hongje 1-Dong, Seodaemun-Gu, Seoul, Korea, on Oct. 18, 2006 (Accession Nos: KCCM10789P and KCCM10788P) and on Jul. 17, 2009 (Accession No. KCCM11018P).

Example 2

Expression of the Recombinant Arabinose Isomerase in *Bacillus*

The recombinant strain *Bacillus subtilis* GSAIB-1 (KCCM10788P) prepared in the above Example 1 was inoculated in LB medium (Bacto-trypton 10 g/L, Bacto-yeast extract 5 g/L, NaCl 10 g/L) containing 20 µg/Ml of chloramphenicol, followed by shaking-culture at 230 rpm and 37° C. for 12 hours, resulting in the pre-culture solution. The pre-culture solution was inoculated in the main culture medium having the same composition at the concentration of 0.1%, followed by shaking-culture at 230 rpm and 37° C. until $OD_{600}$ reached 1 to induce the expression of the recombinant arabinose isomerase. To measure the enzyme activity of the expressed arabinose isomerase, the culture solution was centrifuged at 12,000×g for 10 minutes and cells were recovered. The cells were resuspended in 50 mM Tris-HCl (pH 8.2) buffer, followed by ultrasonification (170 Watt, cooling with ice at intervals of 1 second/2 minutes) to lyse the cells. Centrifugation was performed again at 12,000×g for 12 minutes to induce isomerization of galactose using the supernatant as a crude enzyme solution.

The isomerization of galactose was performed with a mixture of 25 µl of 100 mM galactose and 100 µl of the crude enzyme solution as a substrate at 60° C. for 1 hour. To measure the activity of galactose isomerization, 100 µl of the crude enzyme solution containing 40 mM of galactose as a substrate was mixed with 1 Ml of reaction buffer (50 mM Tris-HCl, pH 7.0), followed by reaction at 65° C. for 20 minutes. At that time, 5 mM of $MgCl_2$ and 1 mM of $MnCl_2$ were added to the reaction mixture. The activity of the isomerase was measured by the cystein-carbazol-sulfuric acid method (Dische, Z., and E. Borenfreund., A New Spectrophotometric Method for the Detection and Determination of Keto Sugars and Trioses, J. Biol. Chem., 192:583-587, 1951). The protein contained in the crude enzyme solution was quantified with a Bradford assay kit (Biorad, U.S.A.). As a result, the isomerase activity was 0.2045±0.0078 (mg-tagatose/mg-protein·h), indicating that the product of galactose isomerization, tagatose, was successfully generated (FIG. 3).

To provide optimum conditions for enzyme expression according to the composition of each culture solution, MB (Bacto-trypton 10 g/L, Bacto-yeast extract 5 g/L, NaCl 10 g/L, Soytone 10 g/L) and LB (Bacto-trypton 10 g/L, Bacto-yeast extract 5 g/L, NaCl 10 g/L) media, which have been generally used for the culture of *Bacillus*, were used as basic media. The recombinant strain GSAIB-1 was inoculated in LB medium (Bacto-trypton 10 g/L, Bacto-yeast extract 5 g/L, NaCl 10 g/L) containing chlorampenicol at the concentration of 20 µg/Ml, followed by shaking-culture at 230 rpm and 37° C. in a shaking incubator for 12 hours. The culture solution was used as a pre-culture solution. The pre-culture solution was inoculated in LB medium containing 10 g/L of carbon source (fructose, glucose, succinate, sorbitol or sucrose) and MB medium (Bacto-trypton 10 g/L, Bacto-yeast extract 5 g/L, NaCl 10 g/L, soytone 10 g/L) at the concentration of 0.1%, followed by shaking-culture at 230 rpm and 37° C. in a shaking incubator until $OD_{600}$ reached 1, which suggests that the expression of the recombinant arabinose isomerase was induced. The expression level of the enzyme in MB medium was 30% lower than that in LB medium. Protein expression patterns according to the different carbon sources added were also investigated, for which industrially acceptable carbon sources such as glucose, fructose, succinate, sorbitol and sucrose were added to LB medium respectively by 10 g/L. The expression level of the enzyme was investigated. As a result, the enzyme expression was slightly increased with the addition of succinate or sorbitol (FIG. 4).

Example 3

Expression of the Recombinant Arabinose Isomerase in *Corynebacterium*

The recombinant strain *Corynebacterium glutamicum* GSAIC-1 (KCCM10789P) and *Corynebacterium glutamicum* mGTAIC001(KCCM11018P) prepared in Example 1 was inoculated in MB medium (Bacto-trypton 10 g/L, Bacto-yeast extract 5 g/L, NaCl 10 g/L, Soytone 5 g/L) containing 10 µg/Ml of kanamycin, followed by shaking-culture at 200 rpm and 30 in a shaking incubator for 24 hours to prepare a pre-culture solution. The obtained pre-culture solution was inoculated in a main culture medium at the concentration of 1%, followed by shaking-culture at 200 rpm and 30 in a shaking incubator until $OD_{600}$ reached 0.1 to induce expression of the recombinant arabinose isomerase. To measure the enzyme activity of the expressed arabinose isomerase, the culture solution was centrifuged at 8000×g for 10 minutes and cells were recovered. The cells were resuspended in 50 mM Tris-HCl (pH 7.0) buffer solution, followed by ultrasonification to lyse the cells. Centrifugation was performed again at 8000×g for 12 minutes to induce isomerization of galactose using the supernatant as a crude enzyme solution. The protein included in the crude enzyme solution was quantified with a Bradford assay kit (Biorad, U.S.A.). As a result, the isomerase activity were each 1.387 and 1.849 (mg-tagatose/mg-protein·h), indicating that the product of galactose isomerization, tagatose, was successfully generated. Furthermore, the activity of enzyme originated from *Geobacillus thermodenitrificans* is higher than that originated from *Geobacillus stearothermophilius*.

To optimize the expression of arabinose isomerase in the recombinant *Corynebacterium glutamicum* GSAIC-1, the recombinant strain was inoculated in MB medium (Bacto-trypton 10 g/L, Bacto-yeast extract 5 g/L, NaCl 10 g/L, Soytone 5 g/L) containing 10 µg/Ml of kanamycin at the concentration of $OD_{600}$=0.6, resulting in the preparation of a pre-culture solution. The growth of the *Corynebacterium* strain in the two basic media for the culture, MB medium (Bacto-trypton 10 g/L, Bacto-yeast extract 5 g/L, NaCl 10 g/L, Soytone 5 g/L) and the modified medium (Bacto-peptone 10 g/L, Bacto-yeast extract 5 g/L, NaCl 2.5 g/L, Beef extract 5 g/L), was investigated. Temperature dependent (25, 30, 37), pH dependent, glucose (carbon source) and sucrose concentration dependent growths in the two media were compared. In addition, the growths under stationary and aerobic conditions were also compared. The growths under the various conditions and the expression levels of the enzyme thereby were measured every hour to judge the optimum expression conditions for mass-production of the recombinant arabinose isomerase (Tables 2 and 3).

TABLE 2

|  | Modified medium | MB medium | | | |
|---|---|---|---|---|---|
|  | Aerobic | Stationary | Aerobic 25 | 30 | 37 |
| $OD_{600}$ | 5.66 | 9.0 | 9.34 | 7.44 | 9.34 | 4.64 |
| pH | 7.6 | 7.8 | 7.6 | 7.5 | 7.6 | 7.6 |
| Activity (mU/ml) | 21.859 | 29.008 | 31.639 | 30.826 | 31.639 | 25.833 |

TABLE 3

|  | Sucrose | | | | | Glucose |
|---|---|---|---|---|---|---|
|  | 0% | 2.5% | 5% | 7.5% | 10% | 10% |
| $OD_{600}$ | 9.68 | 9.7 | 11.84 | 10.36 | 10.14 | 5.76 |
| pH | 7.6 | 4.7 | 4.4 | 4.4 | 4.6 | 4.4 |
| Activity (mU/ml) | 31.6 | 56.979 | 41.764 | 51.198 | 46.003 | 23.236 |
| Activity (mU/ml) | 31.6 | 56.979 | 41.764 | 51.198 | 46.003 | 23.236 |

To measure the enzyme activity of the recombinant arabinose isomerase, the enzyme was treated and quantified in the same manner as described in Example 2. When cells were cultured at 30 under aerobic conditions with the addition of 2.5% sucrose, tagatose showed approximately 57.0 mU/ml of enzyme activity which is 1.8 fold higher than that observed in the standard culture (31.6 mU/ml), suggesting that the enzyme activity increased with the increase in the growth of the cells. The cell growth results in the optimum medium are shown in FIG. 5.

Example 4

Separation and Purification of the Recombinant Arabinose Isomerase

To optimize the expression of arabinose isomerase in the recombinant *Corynebacterium glutamicum* mGTAIC001, 2 L culture of the recombinant strain was performed under the optimum culture conditions determined in the above Example 3. The culture solution was centrifuged at 8000×g for 10 minutes and cells were recovered. The cells were resuspended in 50 mM Tris-HCl (pH 7.0) buffer, and used for the protein purification. The cell suspension progressed to cell lysis using a high pressure cell homogenizer T-series (4.0 kW; Constant systems, UK), followed by heat-treatment at 80 for 20 minutes. Centrifugation was performed at 10,000×g for 10 minutes to separate the expressed recombinant thermophilic arabinose isomerase.

The separated recombinant enzyme solution was filtered by ultrafiltration (MW: 10,000; Sartorius, U.S.A.) and was purified by Q Sepharose Fast Flow (anion exchange column) (staring buffer: 20 mM Tris-HCl, pH 7.5, elution buffer: 20 mM Tris-HCl (pH 7.5)+500 mM NaCl). The protein was purified by FPLC system and it was analyzed by SDS-PAGE. As a result of purification by concentration (30 times) of the enzyme solution, the many impurities were observed in it at the heat treatment stage, but the relatively few impurities were observed in the final enzyme solution which passed through Q Sepharose Fast Flow (anion exchange column).

The activity of the enzyme was measured by the cystein-carbazol-sulfuric acid method (Dische, Z., and E. Borenfreund., A New Spectrophotometric Method for the Detection and Determination of Keto Sugars and Trioses, *J. Biol. Chem.*, 192:583-587, 1951). The fraction contained in the enzyme solution was analysed by SDS-PAGE. The dialysis was performed by using the fraction having the highest purity (20 mM Tris-HCl (pH7.5), MWCO=8,000 (Spectra/Por membrane, SPECTRUM Lab. Inc.)).

Example 5

Biochemical Characteristics of Recombinant Arabinose Isomerase

The recombinant arabinose isomerase expressed in the *Corynebacterium glutamicum* mGTAIC001 prepared in Example 4 was identified.

1) Optimization of Temperature

To measure the optimum temperature, the purified arabinose isomerase originated from the *Corynebacterium glutamicum* mGTAIC001 was added in the substrate (100 mM galactose). The activity of the enzyme was measured in the reaction buffer (50 mM Tris-HCl, pH 7.0, 1 mM $MnCl_2$ was added) at 55° C. to 85° C. (at intervals of 5° C.). The activity of the enzyme was measured by the cystein-carbazol-sulfuric acid method (Dische, Z., and E. Borenfreund., A New Spectrophotometric Method for the Detection and Determination of Keto Sugars and Trioses, *J. Biol. Chem.*, 192:583-587, 1951).

As a result, the optimum temperature of arabinose isomerase is 70° C. (FIG. 6).

2) Thermal Stability

To measure the thermal stability, 0.05 mg purified arabinose isomerase originated from the *Corynebacterium glutamicum* mGTAIC001 was incubated in the water-bath at 60° C. to 80° C. for 180 min (at intervals of 5° C.). Also, the thermal stability was confirmed with and without 1 mM $MnCl_2$ which is cofactor. The sampling was performed at the appointed time, and the retained activity of the arabinose isomerase was measured by using it. As a result of Half-life measurement according to with and without $MnCl_2$, the enzyme activity is very stable when $MnCl_2$ is added, but the shorter Half-life of an enzyme activity is observed when $MnCl_2$ is not added than the above condition. Therefore, these results show that addition of metal ion is very effective to improve the stability of enzyme (FIG. 7).

[표4] Half-life ($t_{1/2}$, min) of mGTAIC001 at different temperatures

| cofactor | sample | 60° C. | 65° C. | 70° C. | 75° C. | 80° C. |
|---|---|---|---|---|---|---|
| present $MnCl_2$ [1 mM] | m GTAI | $ND^a$ | $ND^a$ | $ND^a$ | 26.4 | $NA^b$ |
| absent $MnCl_2$ | m GTAI | $ND^a$ | 818.5 | 150.6 | 20 | $NA^b$ |

$ND^a$: Not detectable (very stable)
$NA^b$: Not activity

3) Metal Ion Effect

In order to investigate the metal ion effect in the activity and thermal stability of enzyme, the change of enzyme activity was measured to the purified arabinose isomerase originated from *Corynebacterium glutamicum* mGTAIC001.

All of metal ion was removed from the arabinose isomerase using 10 mM EDTA. The test was performed by adding the arabinose isomerase which was added in the substrate (100 mM galactose) in 50 mM Tris-HCl buffer at 70° C. for 30 min at pH 7.0. The change of enzyme activity was determined by adding 1 mM of various metal ion. As a result, $Mn^{2+}$, $Co^{2+}$ ion are shown to the relative increase of enzyme activity and $Mn^{2+}$ ion is shown to the maximum enzyme activity (FIG. 8).

4) Optimum pH

To measure the optimum pH, the activity of arabinose isomerase was measured by changing the range of pH 4 to 9. The test was performed by adding 100 mM galactose, 1 mM $MnCl_2$ and the arabinose isomerase at 70° C. for 30 min at various pH value.

The reaction buffer were follows: 50 mM Sodium acetate (pH4-5), 50 mM Sodium phosphate (pH6-7), 50 mM Tris-Cl (pH7-8), respectively. As a result, the optimum pH is 7.4 (FIG. 9)

5) Enzyme Kinetics

To measure the enzyme kinetics of purified arabinose isomerase of the present invention, kinetic parameters were determined at 60° C., 65° C. and 70° C. (table 5).

As a result, $K_m$ values which is affinity of binding between the enzyme and its substrate were increased by 2.4 times at 65° C. (161.mM), 70° C. (161.7 mM) than 60° C. (67 mM). From the above result, it can be seen that binding affinity of substrate is low when the temperature is high. The $V_{max}$ value which is maximum velocity of the reaction were 2.5 U/mg, 6.5 U/mg and 9.1 U/mg, respectively and it increased by the increasing of reaction temperature. And, $k_{cat}/K_m$ value which is catalytic efficiency were 2.1 $mM^{-1}min^{-1}$, 2.3 $mM^{-1}min^{-1}$ and 3.2 $mM^{-1}min^{-1}$, respectively and it means that the productivity of tagatose was increased by the increasing of reaction temperature.

As shown in the table 6, the yield of tagatose of "*Corynebacterium glutamicum* mGTAIC001" were increased by 2 to 9 times as compared to "*Corynebacterium glutamicum* GSAIC-1"

Example 7

Production of Tagatose by Using Microbial Immobilization

Production of tagatose was performed by using the immobilized recombinant *Corynebacterium glutamicum* mGTAIC001. The method of immobilization used in the present invention is the method of cell entrapment using alginate. As a result of test for optimum amount of crosslinker and strain, it is confirm that immobilized beads can be prepared by using crosslinker 1.5 to 2.5 wt % and strain 35 wt %, respectively A sodium alginate solution with the pellet of strain were prepared by mixing until the final concentration of 2%. The whole cell immobilization alginate beads were prepared by dropping the mixed solution into the 0.1M $CaCl_2$ solution using a needle. Then, the immobilized alginate beads were cured at low temperature for 4 h and finally prepared by swelling in 300 g/L of galactose solution.

400 ml of the immobilized alginate beads were added the glass column and isomerization reaction was performed by passing 300 g/L of galactose substrate solution under 60° C. The resultant was analyzed by HPLC. The glucose solution which was passed through the bioreactor was recycled to the 200 ml of reservoir. As a result, it can be seen that tagatose production is well established (FIG. 10).

TABLE 5

| | | | Properties | | | |
|---|---|---|---|---|---|---|
| AIs | $Temp_{opt}$ (° C.) | $pH_{opt}$ | $t_{1/2}$ (min) | $V_{max}$ (U/mg) | $K^m$ (mM) | $k_{cat}/K_m$ ($mM^{-1}min^{-1}$) |
| mGTAI | 60° C. | 7.0-7.5 | $ND^a$ | 2.5 ± 0.07 | 67.0 ± 2.98 | 2.1 ± 0.04 |
| | 65° C. | | $ND^a$ | 6.5 ± 0.57 | 161.1 ± 16.38 | 2.3 ± 0.03 |
| | 70° C. | | $ND^a$ | 9.1 ± 1.42 | 161.7 ± 27.00 | 3.2 ± 0.04 |

Example 6

Production of Tagatose Using the Recombinant GRAS Strain of the Present Invention Culturing was performed in the same manner as in the example 2 and 3. After the pretreatment of culture medium, 20% of *Bacillus subtilis* GSAIB-1, *Corynebacterium glutamicum* GSAIC-1 and *Corynebacterium glutamicum* mGTAIC001 was respectively inoculated into 300 g/L of galactose solution. Then, tagatose productivity with respect to fermentation time were measured at 65° C. for 3 h, and the results are shown in table 6.

TABLE 6

| | (unit: g/L) | | |
|---|---|---|---|
| Reaction time between the reaction time (hr) | GSAIB001 | GSAIC001 | mGTAIC001 |
| 3 | 8.23 | 27.16 | 58.62 |

In order to confirm the enzyme conversion reaction of tagatose in the bioreactor, the bioreactor was operated continuously during a couple of days. 300 g/L galactose solution as a prepared substrate solution was continuously passed through the bioreactor at 100 ml/h. As a result, the production activity of tagatose was stably maintained after 10 days later (FIG. 11).

INDUSTRIAL APPLICABILITY

As explained hereinbefore, the present inventors confirmed that arabinose isomerase originated from the thermophilic *Geobacillus* sp. in the present invention was successfully and stably expressed in GRAS strains, *Corynebacterium* sp. strain and *Bacillus* sp. strain. Accordingly, the present invention provides an active recombinant enzyme and a method of preparing tagatose which contains the step of an efficient immobilizing continuous reaction using the same. It is essential for a food additive to be safe, particularly in the production of biotechnological food using a microorganism enzyme. According to the present invention, arabinose isomerase originating from the *Geobacillus* sp. strain was confirmed to be of a safe food grade, so that it could be expressed and consecutively applied to industrialization.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A method of preparing food grade tagatose comprising culturing an immobilized cell of a recombinant GRAS (Generally recognized as safe) strain that expresses thermophilic arabinose isomerase in an active form after transformation with an expression vector which contains a gene encoding the thermophilic arabinose isomerase originating from a thermophilic *Geobacillus* sp. and contacting the cultured immobilized cell with a substrate that is converted into tagatose by the thermophilic arabinose isomerase, wherein the expression vector is shuttle vector pHT01 originating from *Bacillus* sp. or shuttle vector pCJ-1 originating from *Corynebacterium* sp.

2. The method of preparing food grade tagatose according to claim 1, wherein the *Geobacillus* sp. is *Geobacillus stearothermophilus* DSM22 or *Geobacillus thermodenitrificans*.

3. The method of preparing food grade tagatose according to claim 1, wherein the gene encoding the thermophilic arabinose isomerase has the nucleotide sequence of the product of a polymerase chain reaction performed using template genomic DNA extracted from *Geobacillus stearothermophilus* DSM22 and using primers oligonucleotides having the sequence of SEQ ID NO: 1 and SEQ ID NO: 2, or the nucleotide sequence of the product of a polymerase chain reaction performed using template genomic DNA extracted from *Geobacillus stearothermophilus* DSM22 and using primers oligonucleotides having the sequence of SEQ ID NO: 3 and SEQ ID NO: 4.

4. The method of preparing food grade tagatose according to claim 1, wherein the GRAS strain is *Corynebacterium* sp. or *Bacillus* sp.

5. The method of preparing food grade tagatose according to claim 4, wherein the *Bacillus* sp. is *Bacillus subtilis* 168.

6. The method of preparing food grade tagatose according to claim 4, wherein the *Bacillus* sp. is *Bacillus subtilis* GSAIB-1(KCCM-10789P).

7. The method of preparing food grade tagatose according to claim 4, wherein the *Corynebacterium* sp. is *Corynebacterium glutamicum* ATCC12032.

8. The method of preparing food grade tagatose according to claim 4, wherein the *Corynebacterium* sp. is *Corynebacterium glutamicum* GSAIC-1 (KCCM-10788P).

9. The method of preparing food grade tagatose according to claim 4, wherein the *Corynebacterium* sp. is *Corynebacterium glutamicum* mGTAIC001(KCCM-11018P).

* * * * *